United States Patent
Yang et al.

(10) Patent No.: US 8,409,205 B2
(45) Date of Patent: Apr. 2, 2013

(54) FIXATION DEVICE FOR INTRAMEDULLARY NAIL

(75) Inventors: Libo Yang, Changzhou (CN); Weidong Shan, Changzhou (CN); Zhimin Wang, Changzhou (CN); Tong Wang, Changzhou (CN); Kang Yang, Changzhou (CN); Qingxing Jiang, Changzhou (CN); Wei Ding, Changzhou (CN); Aiping Wang, Changzhou (CN); Kai Jiang, Changzhou (CN); Jianpei Cui, Changzhou (CN); Hao Peng, Changzhou (CN)

(73) Assignee: Changzhou Kanghui Medical Innovation Co., Ltd., Changzhou (CN)

( * ) Notice: Subject to any disclaimer, the term of this patent is extended or adjusted under 35 U.S.C. 154(b) by 0 days.

(21) Appl. No.: 13/349,542

(22) Filed: Jan. 12, 2012

(65) Prior Publication Data

US 2012/0116400 A1 May 10, 2012

Related U.S. Application Data

(63) Continuation of application No. PCT/CN2010/074207, filed on Jun. 22, 2010.

(30) Foreign Application Priority Data

Jul. 14, 2009 (CN) .......................... 2009 1 0031807

(51) Int. Cl.
*A61B 17/56* (2006.01)

(52) U.S. Cl. .......................................................... 606/64
(58) Field of Classification Search .............. 606/62–68, 606/86 R
See application file for complete search history.

(56) References Cited

U.S. PATENT DOCUMENTS

| | | | |
|---|---|---|---|
| 6,261,290 B1 * | 7/2001 | Friedl ............................. | 606/64 |
| 2004/0158249 A1 * | 8/2004 | Roth et al. ...................... | 606/62 |
| 2007/0162011 A1 * | 7/2007 | Leyden et al. .................. | 606/65 |

* cited by examiner

*Primary Examiner* — Eduardo C Robert
*Assistant Examiner* — Tara Carter
(74) *Attorney, Agent, or Firm* — Matthias Scholl P.C.; Matthias Scholl

(57) ABSTRACT

A fixation device for an intramedullary nail for proximal femoral fractures, including a main intramedullary nail, a combined locking nail, and cortical bone screws. The main intramedullary nail has a longitudinal axis, a proximal end, and a distal end with a tip. The proximal end includes a through hole for assembling the combined locking nail. The distal end includes an oblong through hole and a circular through hole, both for receiving the cortical bone screws. The combined locking nail includes a head, a distal end of the locking nail, a sleeve, a connecting block, and a cover cap. The connecting block includes a left-handed external thread. The cover cap includes a left-handed internal thread matching with the external thread of the connecting block, a symmetrical sliding plane, and a protrusion block disposed at the end of the symmetrical sliding plane.

1 Claim, 6 Drawing Sheets

FIXATION DEVICE FOR INTRAMEDULLARY NAIL

CROSS-REFERENCE TO RELATED APPLICATIONS

This application is a continuation of International Patent Application No. PCT/CN2010/074207 with an international filing date of Jun. 22, 2010, designating the United States, now pending, and further claims priority benefits to Chinese Patent Application No. 200910031807.0 filed Jul. 14, 2009. The contents of all of the aforementioned applications, including any intervening amendments thereto, are incorporated herein by reference.

BACKGROUND OF THE INVENTION

The invention relates to a fixation device for an intramedullary nail for proximal femoral fracture.

FIELD OF THE INVENTION

Conventionally, the proximal end of an intramedullary nail is fixed to the femoral neck by a single lag screw. However, for patients with osteoporosis or unstable fractures, the single lag screw may cut the femur and for treatment of intertrochanteric fracture of femur, complications, such as collapse of fractures, cut-out of femoral neck screws, and fracture of femoral shaft near the screw tail, etc., are more likely to arise. If a compression screw cuts the femur, osteoporosis, and fractures, a potential rotation and shearing force may exist. There is another type of intramedullary nail in the art, which is fixed with two screws, one is a lag screw and the other one is an anti-rotation screw. This type of fixation has lower complications, but cut-out of screws still occurs, anti-rotation and angular stability is still insufficient.

SUMMARY OF THE INVENTION

In view of the above-described problems, it is one objective of the invention to provide a fixation device for an intramedullary nail for proximal femoral fracture that can effectively solve the complications and cut-out of screws.

To achieve the above objective, in accordance with one embodiment of the invention, there is provided a fixation device for an intramedullary nail for proximal femoral fractures, comprising a main intramedullary nail, a combined locking nail, and cortical bone screws, wherein the main intramedullary nail has a longitudinal axis, a proximal end, and a distal end with a tip; the proximal end forms an angle with respect to the longitudinal axis and has a component connecting to an inserting device; the proximal end comprises a through hole for assembling the combined locking nail; the through hole has an axis which intersects with the longitudinal axis at an angle of 110°-150°; the distal end comprises a transverse oblong through hole with an axis and a transverse circular through hole with an axis, both for receiving the cortical bone screws;

The combined locking nail comprises a head, a distal end of the locking nail, a sleeve, a connecting block, and a cover cap; the connecting block comprises a left-handed external thread, with one end having a hexagonal hole and the other end having a cylindrical step; the cover cap comprises a left-handed internal thread matching with the external thread of the connecting block, a symmetrical sliding plane, and a protrusion block disposed at the end of the symmetrical sliding plane; a distal end surface of the cover cap is a tooth shape; the head is in the shape of a spiral blade; the distal end of the locking nail is arranged with a step with a right angle incision and comprises a tooth-shaped end surface at the end portion; the cylindrical step of the connecting block engages with the step with a right angle incision of the locking nail's distal end; the locking nail and the connecting block form a whole part along the central line by means of the steps; the sleeve is sheathed outside the distal end of the locking nail and comprises inside a plane for cooperating with the symmetrical sliding plane of the cover cap; the two planes can slide relatively; and the protrusion block can be stuck into the end of the plane inside the sleeve.

In a class of this embodiment, the sleeve cannot rotate around the central line with regard to the head of the combined locking nail after the connecting block is tightened by the threads.

In a class of this embodiment, the spiral blade shaped head has 2-6 edges and the end portion of the head comprises a column with smaller diameter, the step with a right angle incision, and 60° teeth distributed peripherally of the end surface.

In a class of this embodiment, the main intramedullary nail has a cylindrical hole at the proximal end and the cylindrical hole comprises two grooves, coaxial with the hole and longitudinal to the main intramedullary nail.

In a class of this embodiment, the distal end of the main intramedullary nail comprises the transverse circular hole and the transverse oblong hole, both can receive the cortical bone screws and an angle β formed by the axis of the transverse circular/oblong holes and the longitudinal axis is 60°-100°.

In a class of this embodiment, the shape of the through hole of the proximal end of the main intramedullary nail matches the shape of the sleeve of the combined locking nail and the latter can slide longitudinally within the former along the central line but can not rotate around the central line.

The combined locking nail is threadedly combined together by means of the step with a right angle incision at the distal end of the combined locking nail, the protrusion block of the cover cap, and the end of the plane arranged at the inner hole of the sleeve for cooperation with the symmetrical sliding plane; the tooth shape of the cover cap cooperates with the tooth-shaped end surface at the distal end of the combined locking nail; the cross section of the sleeve cooperates with the cross section of the through hole at the proximal end of the main intramedullary nail; when the connecting block of the combined locking nail is threadedly tightened, the distal end of the combined locking nail cannot rotate relative to the through hole at the proximal end of the main intramedullary nail, but can rotate in case when the connecting block of the combined locking nail is not threadedly tightened; the connecting block of the combined locking nail is threadedly tightened by means of the rotation of the connecting block to reach a full contact between the tooth shape of the cover cap and the tooth-shaped end surface at the distal end of the combined locking nail.

Advantaged of the invention are summarized below. Since the new type of combined locking nail is adopted based on the conventional method to achieve anti-rotation and angular stability, it has no additional shortcomings but solves some of the disadvantages of the prior art.

The combined locking nail has the following advantages with respect to its self-locking function and unique spiral blade shaped head: first, it has high stability for bones having osteoporosis. When the spiral blade of the combined locking nail is inserted, maximum compression and perfect anchoring force are ensured because of the bones around the compressive area, wide surface area, and increased core diameter. A strong anti-cutting effect can be achieved even in patients having osteoporosis. Second, spiral blade of the combined locking nail is designed to be cross-shaped. When inserted into the bones, it can compress the bones so as to achieve an ideal anchoring force and angular stability to prevent slipped epiphysis. When the blade is locked, it can effectively prevent the femur from rotating. Furthermore, the head of the combined locking nail is like a long rod and comprises a relatively soft tip, making it simple for the intramedullary nail to be inserted and meanwhile to prevent the stress concentration on bones.

The intramedullary nail having an angle of 5° in the longitudinal direction can be inserted through the intertrochanteric area to reach the marrow cavity at the proximal end of the femur, thus incisions are minimized. The combined locking nail at the distal end of the intramedullary nail is selected between the static and dynamic interlocking status. When the vertically-screwed interlocking nail is the dynamic interlocking, the interlocking nail obliquely screwed is the static interlocking. Moreover, conventional static interlocking can also be selected. Interlocking methods can be decided upon different fracture types, thus more options are available for operation.

In an embodiment of the invention, the first hole at the proximal end of the intramedullary nail is made into a conventional cylindrical hole. Two angular openings in the longitudinal direction of the main intramedullary nail with angle at 100°-130° are provided. In the new embodiment of the invention, self-locking function of the combined locking nail is achieved by cooperation of different components thereof. In the form of self-locking, the left-handed thread is used for force transmission and the tooth-shaped structure for antirotation. The tooth-shaped structure shall have a better strength, preferably a 60° tooth. The cover cap of the combined locking nail is arranged with the protrusion block for restricting the combined locking nail from separation before or after self-locking. The spiral blade head of the combined locking nail is coupled to the externally threaded connecting block by a segment of convex and concave column with a diameter between the external diameter and internal diameter of the combined locking nail and with a strength satisfying the working limit of the combined locking nail. The sleeve of the combined locking nail has a length at 40-80 mm preferably and has the external diameter slightly larger than the exicrcle diameter of the spiral blade of the combined locking nail head.

DETAILED DESCRIPTION OF THE EMBODIMENTS

Figure 1:
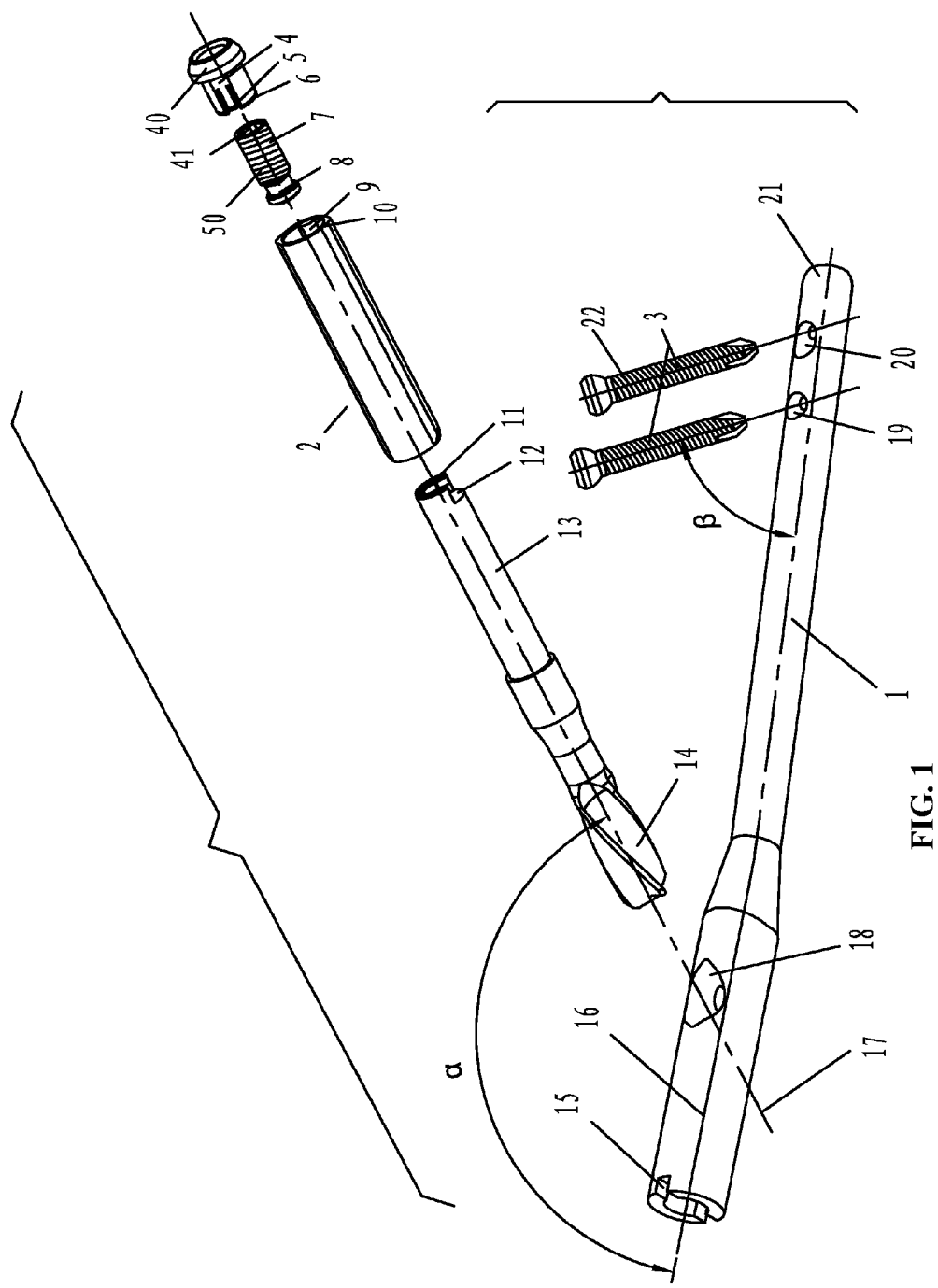
FIG. 1 is an exploded view of a fixation device for an intramedullary nail for proximal femoral fracture in accordance with one embodiment of the invention.

For further illustrating the invention, experiments detailing a fixation device for an intramedullary nail for proximal femoral fracture are described below. It should be noted that the following examples are intended to describe and not to limit the invention.

As shown in FIGS. 1-6, a fixation device for an intramedullary nail for proximal femoral fracture comprises a main intramedullary nail 1, a combined locking nail 2, and cortical bone screws 3. The cortical bone screws 3 have a full thread 22. The main intramedullary nail 1 has a longitudinal axis 16, a proximal end 15, and a distal end 21 with a tip. The proximal end 15 forms an angle with respect to the longitudinal axis 16 and has a component connecting to an inserting device. The proximal end 15 comprises a through hole 18 for assembling the combined locking nail 2. The through hole 18 comprises an axis which intersects with the longitudinal axis 16 at an angle of 110°-150°. The distal end 21 comprises a transverse oblong through hole 20 with an axis and a transverse circular through hole 19 with an axis.

The combined locking nail 2 comprises a head 14, a distal end 13 of the locking nail, a sleeve 10, a connecting block 50, and a cover cap 40. The cover cap 40 is provided with an internal thread matching with an external thread 7 of the connecting block 50, a symmetrical sliding plane 4, and a protrusion block 5. The distal end surface of the cover cap 40 has a tooth shape 6. The head 14 is in a shape of a spiral blade. The distal end 13 of the locking nail is arranged with a step with a right angle incision 12 and comprises a tooth-shaped end surface at the end portion. The protrusion block 5 is arranged on the cover cap 40. A left-handed external thread 7 is arranged on the connecting block 50 with one end having a hexagonal hole 41 and the other end having a cylindrical step 8. The cylindrical step 8 of the connecting block engages with the step with a right angle incision of the locking nail's distal end 13 and then they form a whole part along the central line 17 by means of the steps. The sleeve 10 is sheathed outside the distal end 13 of the locking nail and comprises inside a plane 9 for cooperating with the symmetrical sliding plane 4 of the cover cap 40 for relative slide. The protrusion block 5 can be stuck into the end of the plane 9 inside the sleeve.

The sleeve 10 cannot rotate around the combined locking nail head 14 relative to the central line after being sheathed on the connecting block 50 and tightened by the thread.

The spiral blade shaped head 14 has 2-6 edges and the end portion of the head comprises a column with smaller diameter, the step with a right angle incision 12, and 60° teeth distributed peripherally of the end surface.

The main intramedullary nail 1 has a cylindrical hole at the proximal end and the cylindrical hole comprises two grooves, coaxial with the hole and longitudinal to the main intramedullary nail.

The distal end 21 of the main intramedullary nail 1 comprises a circular hole 19 and an oblong hole 20, both can receive the cortical bone screws 3 and the angle β formed between the axis of the circular hole 19, the oblong hole 20 and the longitudinal axis 16 is 60°-100°.

The proximal end of the main intramedullary nail 1 has a through hole 18 matching the shape of sleeve 10 of the combined locking nail 2 and the latter can slide longitudinally within the former along the central line 17 but not rotate around the central line 17.

The combined locking nail 2 is threadedly combined together by means of the step with a right angle incision 12 at distal end of the combined locking nail, the protrusion block 5 on the cover cap 40, and the end of the symmetrical sliding plane 9 arranged at the inner hole of the sleeve 10. The tooth shape 6 of the end surface of the cover cap 40 can cooperate with the tooth-shaped end surface 11 at the distal end 13 of the combined locking nail, and the cross section of the sleeve 10 can cooperate with the cross section of the through hole 18 at the proximal end of the main intramedullary nail. When the threaded connecting block 50 of the combined locking nail is threadedly tightened, the distal end 14 of the combined locking nail 2 relative to the through hole 18 at the proximal end of the main intramedullary nail cannot be rotated, but can rotate in case the connecting block 50 of the combined locking nail is not threadedly tightened. The threaded connecting block 50 of the combined locking nail is threadedly tightened by means of the rotation of the connecting block 50 enabling full contact between the tooth shape 6 on the cover cap 40 and the tooth-shaped end surface 11 at the distal end 13 of the combined locking nail.

Figure 6:
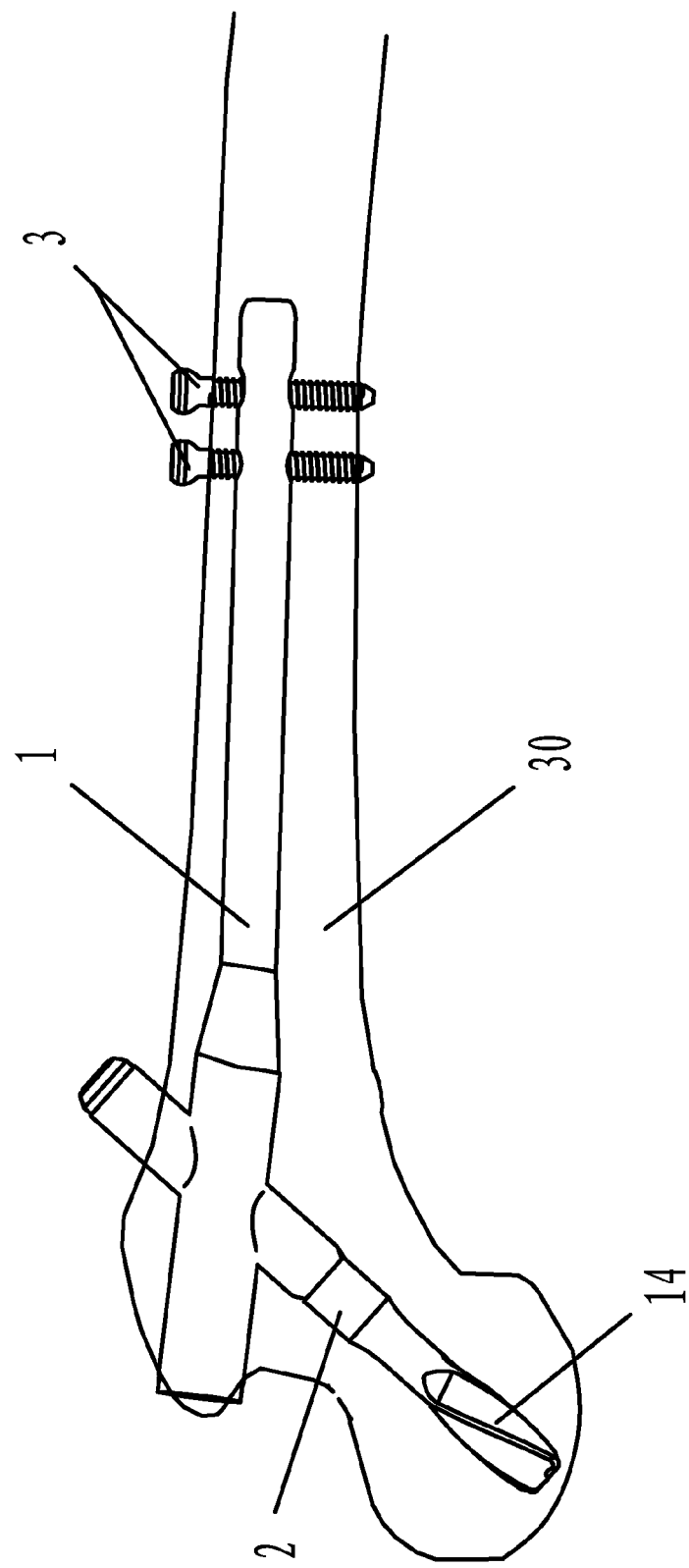
FIG. 6 is a perspective view of a fixation device for an intramedullary nail for proximal femoral fracture after being embedded and fixed within the femur in accordance with one embodiment of the invention.

As shown in FIG. 1 and FIG. 6, the intramedullary nail 1 comprises a proximal end 15, a longitudinal axis 16, and a distal end 21. The distal end 21 is used for receiving the cortical bone screws. The intramedullary nail 1 also comprises a through hole 18, having a central line 17, which is close to the proximal end 15 and transversely intersected with the longitudinal axis 16. The through hole is used to receive the femoral head screw, i.e. the combined locking nail. The central line 17 of the through hole 18 transversely intersects with the longitudinal axis 16 to form an obtuse angle α of 110°-150° or an acute angle of 180°-α, i.e., 30°-70°. The distal end of the intramedullary nail has two transverse holes, parallel with one another and perpendicular to the longitudinal axis of the intramedullary nail 1. The first hole closer and the second hole farther to the distal end 21 is the oblong hole 20 and the circular hole 19, respectively, having the same diameter. The oblong hole has the length of 2-5 mm. Both holes are used to receive the cortical bone screws.

Figure 2:
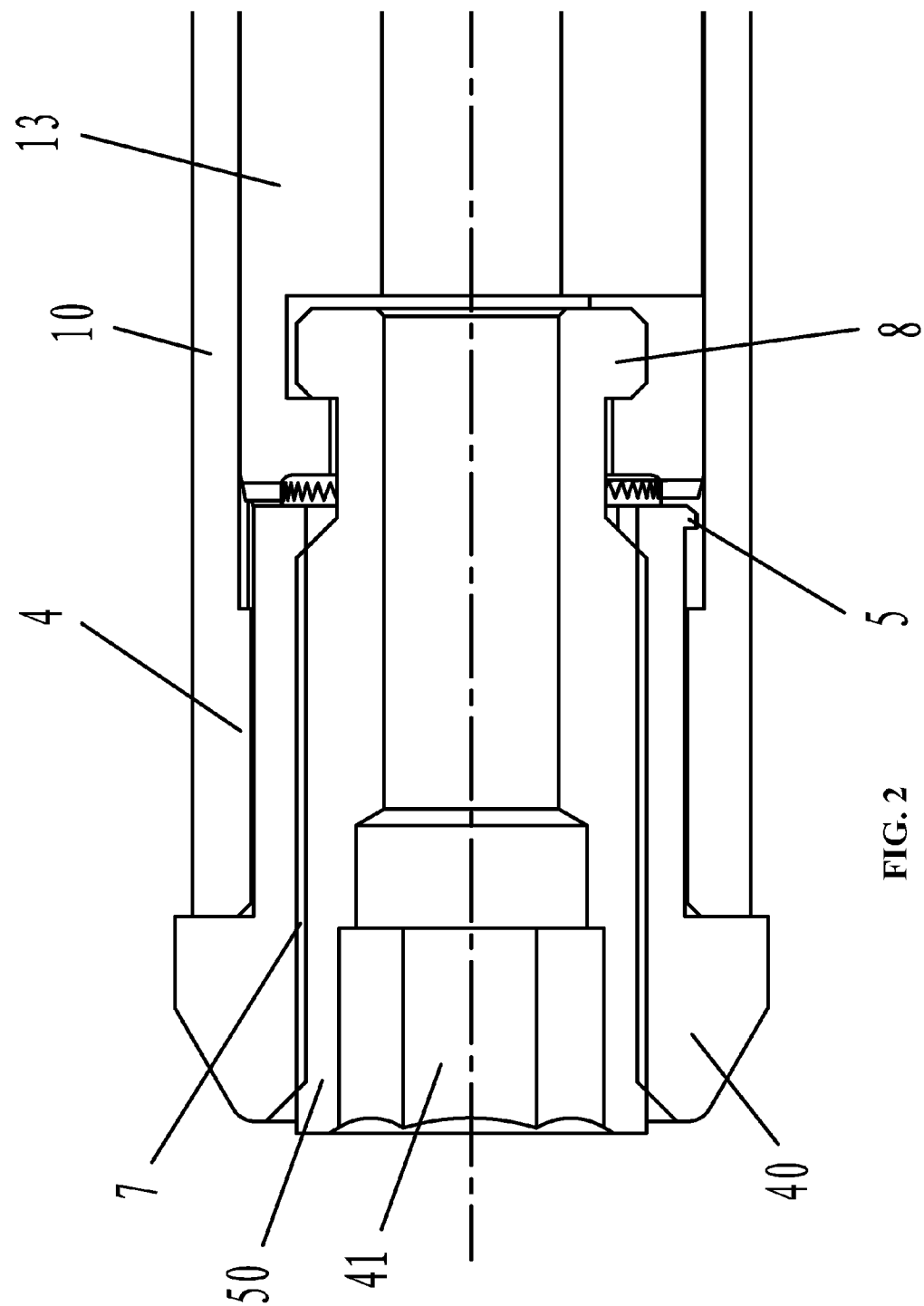
FIG. 2 is a partial sectional view of a combined locking nail of a fixation device for an intramedullary nail for proximal femoral fracture in accordance with one embodiment of the invention.
Figure 5:
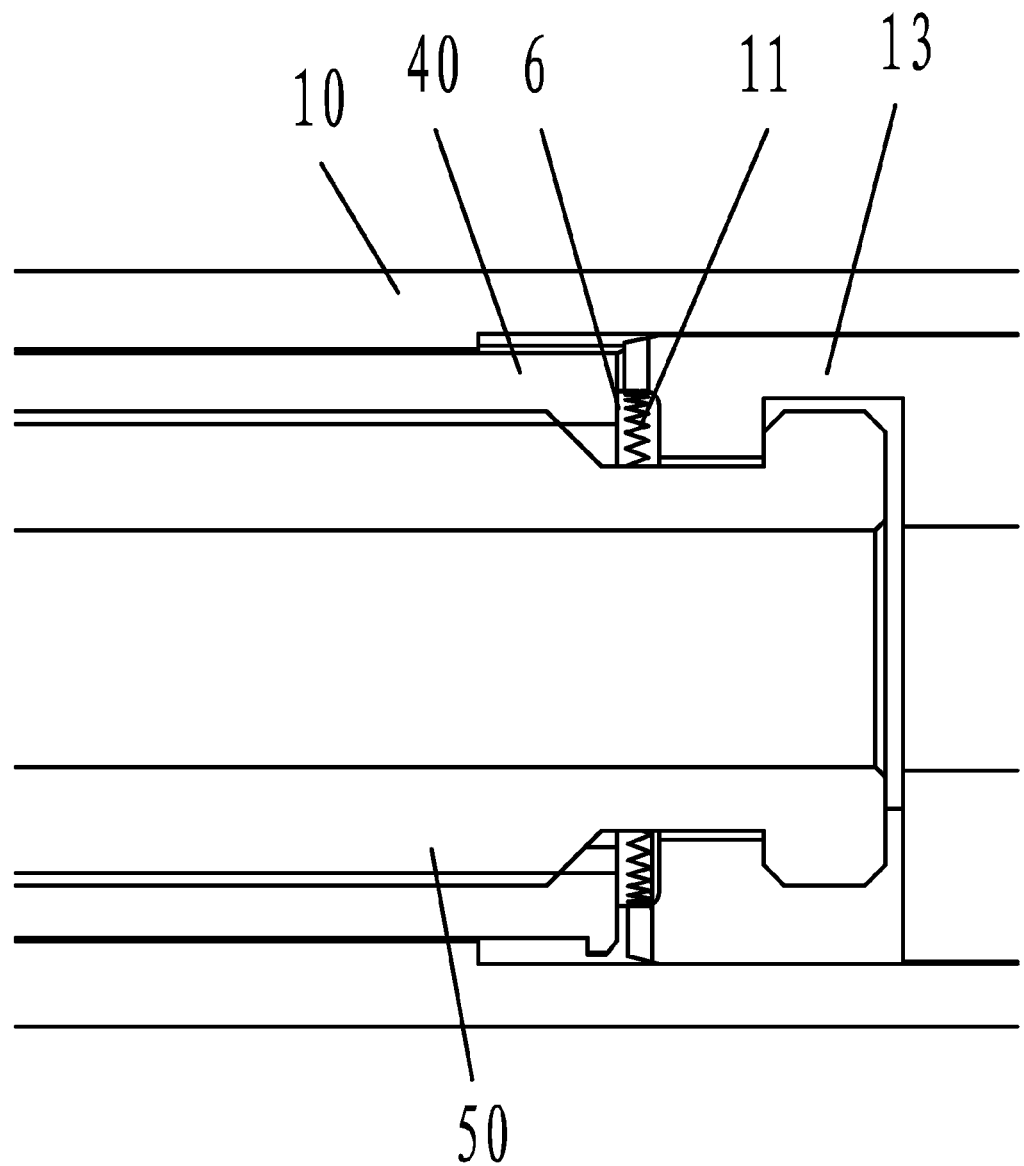
FIG. 5 is a schematic diagram of the engagement of upper and lower teeth after locking of a combined locking nail of a fixation device for an intramedullary nail for proximal femoral fracture in accordance with one embodiment of the invention.

As shown in FIGS. 1, 2, and 5, the inner structure of the combined locking nail 2 is as follows: the cover cap 40 engages with the connecting block 50 by a left-handed thread, the connecting block 50 is separated with the sleeve 10 by the protrusion block 5, the connecting block 50 is coupled to the distal end 13 by the cylindrical step 8, two end surfaces between the cover cap 40 and the distal end 13 comprise the tooth-shaped end surface 11, the sleeve 10 is covered on the end portion of the distal end 13. One end of the cover cap 40 has the hexagonal hole 41 or a quadrilateral hole, one side of the symmetrical sliding plane has the protrusion block 5 that is 0.5 mm higher than the plane, two sides of the protrusion block 5 each has a longitudinal groove with a width of approx. 0.5 mm and a length 6 mm. The end portion of the distal end 13 has the step 12, whose lower end has an inner hole for receiving the cylindrical step 8 of the connecting block 50, so that the cylindrical step 8 of the connecting block 50 can be inserted transversely through the step 12 to couple the connecting block 50 in the longitudinal direction.

Figure 3:
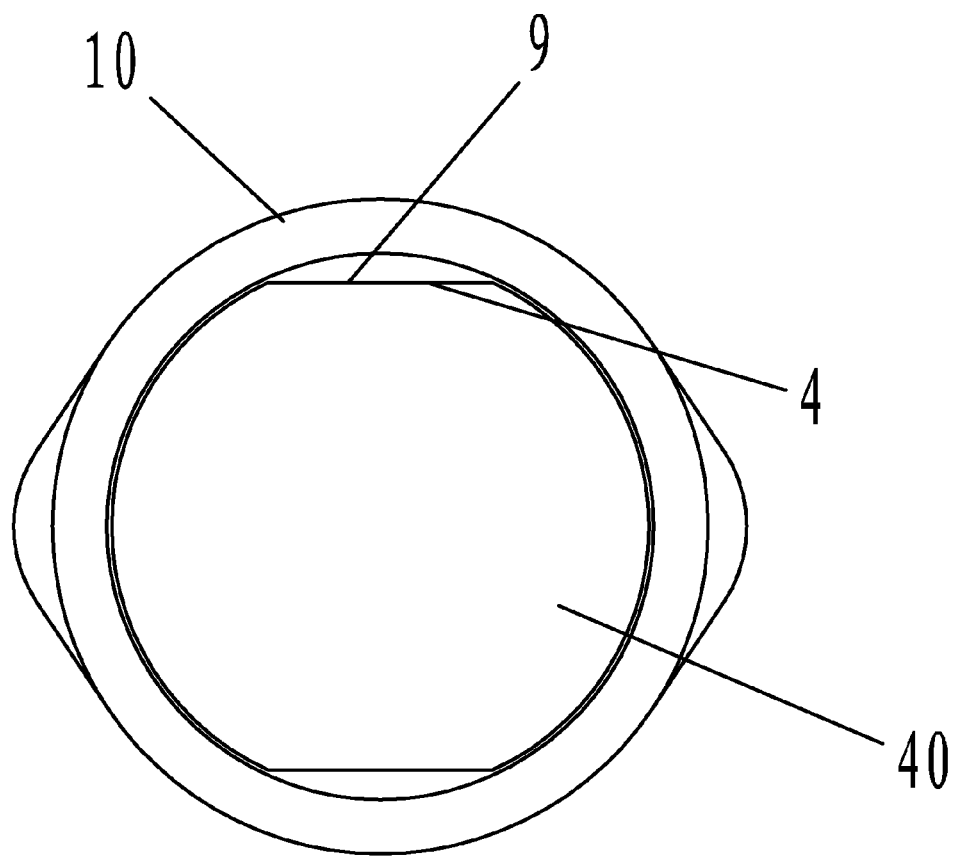
FIG. 3 is a sectional view of a sleeve of a combined locking nail of a fixation device for an intramedullary nail for proximal femoral fracture in accordance with one embodiment of the invention.
Figure 4:
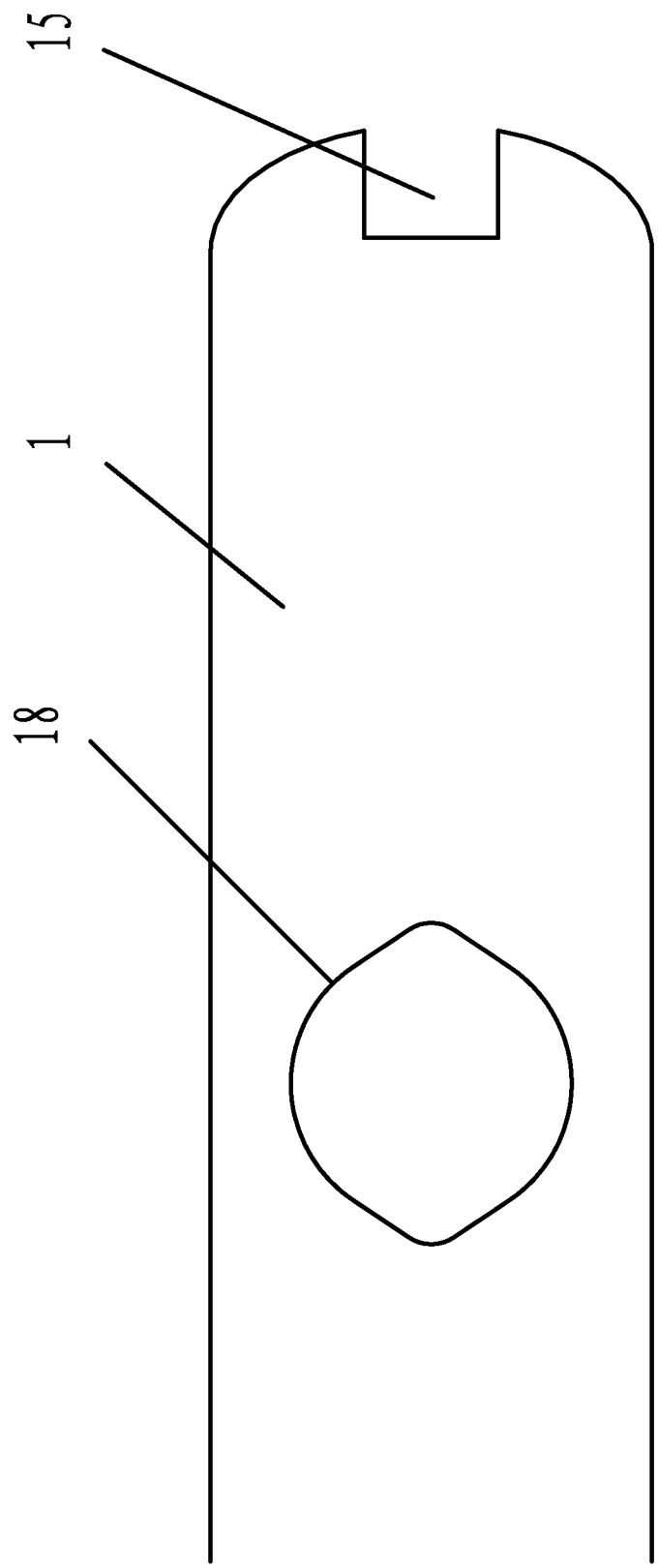
FIG. 4 is a longitudinal view of a proximal end hole of an intramedullary nail of a fixation device for an intramedullary nail for proximal femoral fracture in accordance with one embodiment of the invention.

As shown in FIG. 3 and FIG. 4, the shape of the through hole 18 at the proximal end of the intramedullary nail 1 is consistent with the section shape of the sleeve 10 of the combined locking nail 2. The section dimension of the sleeve 10 is slightly smaller than the size of the through hole 18 allowing the intramedullary nail to receive the combined locking nail. The through hole 18 at the proximal end of the intramedullary nail 1 and the sleeve 10 of the combined locking nail 2 can only slide along the central line 17 but not for relative rotation.

The following is a brief description of the intramedullary nailing for surgery:

1. Carry out preparation work on marrow cavity of the femur to be operated;
2. Use related tools to insert the intramedullary nail into the marrow cavity;
3. Insert a guide pin into the through hole 18 at the proximal end of the intramedullary nail 1;
4. Drill a hole on the bone for receiving the combined locking nail 2;
5. Insert the combined locking nail 2 that is not self-locked into the femur through the drilled hole and the femur relative to the intramedullary nail cannot be moved after the combined locking nail 2 is threadedly locked; and
6. Drill holes for fixing the intramedullary nail 1 in the distal end and insert cortical bone screws 3 into the circular hole 19 or the oblong hole 20 at the distal end of the intramedullary nail 1.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A fixation device for an intramedullary nail for proximal femoral fractures, the device comprising:
   a) a main intramedullary nail;
   b) a combined locking nail; and
   c) cortical bone screws;
   wherein
   the main intramedullary nail has a longitudinal axis, a proximal end, and a distal end with a tip; the proximal end forms an angle with respect to the longitudinal axis and has a component connecting to an inserting device; the proximal end comprises a through hole for assembling the combined locking nail; the through hole has an axis which intersects with the longitudinal axis at an angle of 110°-150°; the distal end comprises a transverse oblong through hole with an axis and a transverse circular through hole with an axis, both for receiving the cortical bone screws;
   the combined locking nail comprises a head, a distal end of the locking nail, a sleeve, a connecting block, and a cover cap; the connecting block comprises a left-handed external thread, with one end having a hexagonal hole and the other end having a cylindrical step; the cover cap comprises a left-handed internal thread matching with the external thread of the connecting block, a symmetrical sliding plane, and a protrusion block disposed at the end of the symmetrical sliding plane, the protrusion block having two sides; one end of the cover cap has a hexagonal hole or a quadrilateral hole; the protrusion block extends 0.5 mm higher than the symmetrical sliding plane, and each of the two sides of the protrusion block has a longitudinal groove with a width of 0.5 mm and a length of 6 mm; a distal end surface of the cover cap comprises a tooth shape; the head is in the shape of a spiral blade; the distal end of the locking nail is arranged with a step with a right angle incision and comprises a tooth-shaped end surface at the end portion; the cylindrical step of the connecting block engages with the step with a right angle incision of the locking nail's distal end; the locking nail and the connecting block form a whole part along the central line by means of the steps; the sleeve is sheathed outside the distal end of the locking nail and comprises inside a plane for cooperating with the symmetrical sliding plane of the cover cap; the two planes can slide relatively; and the protrusion block can be stuck into the end of the plane inside the sleeve; and the combined locking nail is threadedly combined together by means of the step with a right angle incision at the distal end of the combined locking nail, the protrusion block of the cover cap, and the end of the plane inside the sleeve for cooperation with the symmetrical sliding plane; the tooth shape of the cover cap cooperates with the tooth-shaped end surface at the distal end of the combined locking nail; the cross section of the sleeve cooperates with the cross section of the through hole at the proximal end of the main intramedullary nail; and when the connecting block of the combined locking nail is threadedly tightened, the distal end of the combined locking nail cannot rotate relative to the through hole at the proximal end of the main intramedullary nail, but can rotate in case the connecting block of the combined locking nail is not threadedly tightened.

* * * * *